United States Patent
Haj-Ahmad

(10) Patent No.: US 10,287,625 B2
(45) Date of Patent: May 14, 2019

(54) METHODS AND KITS FOR SEPARATING NUCLEIC ACIDS BY SIZE

(71) Applicant: Norgen Biotek Corp., Thorold, Ontario (CA)

(72) Inventor: Yousef Haj-Ahmad, St. Catharines (CA)

(73) Assignee: Norgen Biotek Corp., Thorold, Toronto (CA)

( * ) Notice: Subject to any disclaimer, the term of this patent is extended or adjusted under 35 U.S.C. 154(b) by 89 days.

(21) Appl. No.: 15/460,489

(22) Filed: Mar. 16, 2017

(65) Prior Publication Data

US 2017/0268047 A1 Sep. 21, 2017

Related U.S. Application Data

(60) Provisional application No. 62/310,368, filed on Mar. 18, 2016.

(51) Int. Cl.
| | | |
|---|---|---|
| *C12Q 1/68* | (2018.01) | |
| *C07H 21/00* | (2006.01) | |
| *G01N 1/34* | (2006.01) | |
| *C12Q 1/6811* | (2018.01) | |
| *C12N 15/10* | (2006.01) | |
| *C12Q 1/6806* | (2018.01) | |

(52) U.S. Cl.
CPC ........ *C12Q 1/6811* (2013.01); *C12N 15/1006* (2013.01); *C12N 15/1072* (2013.01); *C12Q 1/6806* (2013.01)

(58) Field of Classification Search
CPC ...... C12Q 1/68; C07H 21/00; C12N 15/1003; G01N 1/34
See application file for complete search history.

(56) References Cited

U.S. PATENT DOCUMENTS

| 5,200,022 | A * | 4/1993 | Kong ..................... C30B 25/02 117/95 |
| 6,177,278 | B1 * | 1/2001 | Haj-Ahmad ....... C12N 15/1006 423/345 |
| 6,180,778 | B1 * | 1/2001 | Bastian ............... C12N 15/1006 536/25.3 |
| 6,291,248 | B1 | 9/2001 | Haj-Ahmad |
| 6,383,393 | B1 * | 5/2002 | Colpan ................. C12N 15/101 210/198.2 |
| 7,026,453 | B2 | 4/2006 | Haj-Ahmad |
| 7,431,842 | B2 | 10/2008 | Haj-Ahmad |
| 8,063,199 | B2 | 11/2011 | Haj-Ahmad |
| 8,883,421 | B2 | 11/2014 | McReynolds et al. |
| 9,422,596 | B1 * | 8/2016 | Haj-Ahmad ........... C12Q 1/6806 |
| 9,637,781 | B2 * | 5/2017 | Wang ....................... C12Q 1/25 |
| 2004/0175701 | A1 * | 9/2004 | Haj-Ahmad .......... C01B 32/956 435/6.13 |
| 2005/0026175 | A1 * | 2/2005 | Link .................. C12N 15/1006 435/6.13 |
| 2005/0042660 | A1 * | 2/2005 | Hall, Jr. ............. C12N 15/1006 435/6.13 |
| 2005/0059024 | A1 * | 3/2005 | Conrad .............. C12N 15/1003 435/6.12 |
| 2005/0208510 | A1 * | 9/2005 | Latham .............. C12N 15/1006 435/6.12 |
| 2007/0161004 | A1 * | 7/2007 | Brown .................. C12N 15/111 435/6.14 |
| 2008/0142445 | A1 * | 6/2008 | Haj-Ahmad ........... B01D 15/00 210/660 |
| 2009/0223898 | A1 * | 9/2009 | Haj-Ahmad ........... B01D 24/46 210/639 |
| 2012/0021407 | A1 * | 1/2012 | Haj-Ahmad .......... B01L 3/5021 435/5 |
| 2012/0031407 | A1 | 2/2012 | Shi et al. |
| 2013/0149691 | A1 * | 6/2013 | Haj-Ahmad ........... C09K 15/18 435/2 |
| 2014/0255271 | A1 | 9/2014 | Haj-Ahmad |
| 2014/0272968 | A1 * | 9/2014 | Gundling ............. C12Q 1/6806 435/6.11 |

(Continued)

FOREIGN PATENT DOCUMENTS

CA 2517770 2/2007

OTHER PUBLICATIONS

Alon et al., Barcoding bias in high-throughput multiplex sequencing of miRNA. Genome Research 21 : 1506 (Year: 2011).*
Bellingham et al., Small RNA deep sequencing reveals a distinct miRNA signature released in exosomes from prion-infected neuronal cells. Nucleic Acids Research 40 (21) : 10937 (Year: 2012).*
Creighton et al., Expression profiling of micro RNAs by deep sequencing. Briefings in Bioinformatics 10(5 ) : 490 (Year: 2009).*
Guo et al., A Comprehensive Survey of miRNA Repertoire and 3' addition Events in the Placentas of Patients with Pre-Eclampsia from High-Throughput Sequencing PLoS one (Year: 2011).*

(Continued)

*Primary Examiner* — Ethan C Whisenant
(74) *Attorney, Agent, or Firm* — Coats & Bennett PLLC

(57) ABSTRACT

Disclosed are methods and kits for isolating nucleic acids having a size above a desired cut-off size from a nucleic acid containing sample. The method comprises combining the sample with a binding buffer, alcohol and silicon carbide to provide a binding mixture. Nucleic acids having a size above the desired cut-off size are selectively bound to the silicon carbide. The cut-off size for selective binding to the silicon carbide is determined by the alcohol concentration of the binding mixture. The bound nucleic acids are separated from the remaining sample. The bound nucleic acids are optionally washed and then eluted from the silicon carbide. The kit comprises a buffer binding to be diluted with alcohol to provide an alcohol concentration of about 1 to about 50% (v/v), a wash solution, an elution solution, silicon carbide and instructions for adjusting the alcohol concentration to selectively bind nucleic acids having a size above the desired cut-off size.

20 Claims, 4 Drawing Sheets

Specification includes a Sequence Listing.

(56) References Cited

U.S. PATENT DOCUMENTS

| | | | |
|---|---|---|---|
| 2014/0309130 A1* | 10/2014 | Haj-Ahmad | C12Q 1/6886 506/9 |
| 2015/0105275 A1* | 4/2015 | Wong | C12Q 1/686 506/9 |
| 2016/0024490 A1* | 1/2016 | Sperling | C12Q 1/6806 506/26 |
| 2016/0115471 A1* | 4/2016 | Kim | C12N 15/101 436/94 |
| 2016/0326512 A1 | 11/2016 | Haj-Ahmad | |
| 2016/0333338 A1* | 11/2016 | Haj-Ahmad | C12N 15/1006 |
| 2017/0051359 A1* | 2/2017 | Pegtel | C12Q 1/6809 |
| 2018/0073066 A1* | 3/2018 | Myers | C12N 15/111 |

OTHER PUBLICATIONS

Kim et al., Evaluation of viroid extraction methods and application of a one-step reverse transcription real-time polymerase chain reaction assay (RT-qPCR) for the rapid detection of Chrysanthemum stunt viroid (CSVd) infection. Canadian J. of Plant Pathology 37 (2) : 221 (Year: 2015).*

Mlcochova et al., Urine microRNAs as potential noninvasive biomarkers in urologic cancers. Urologic Oncology : Seminars and Original Investigations 32 : 41.e1 (Year: 2014).*

Morin et al., Application of massively parallel sequencing to microRNA profiling and discovery in human embryonic stem cells. Genome Research 18 : 610 (Year: 2008).*

Patnaik et al.,Factors affecting the yield of microRNAs from laser microdissectates of formalin-fixed tissue sections. BMC Research Notes 5 :40 (Year: 2012).*

Shafer P.T,B., A review of the structure of Silicon Carbide. Atca Cryst. B25, 477 (Year: 1969).*

Silicon, Wikipedia Entry (Year: 2018).*

Silicon Carbide, Wikipedia Entry (Year: 2018).*

Silicon Dioxide, Silica, Wikipedia Entry (Year: 2018).*

Solid Small RNA Expression Kit Applied Biosystems, Copyright 2009. (Year: 2009).*

Vigneault et al.,High-Troughput Multiplex Sequencing miRNA. Current Protocols in Human Genetics Unit 11.12 (Year: 2012).*

* cited by examiner

METHODS AND KITS FOR SEPARATING NUCLEIC ACIDS BY SIZE

RELATED APPLICATION

This application claims priority benefits from U.S. Provisional Patent Application No. 62/310,368 and entitled "Method and Kits for Separating Nucleic Acids by Size", which is incorporated herein by reference in its entirety.

FIELD OF INVENTION

The present invention relates to methods and kits suitable for the size selective isolation of nucleic acids using silicon carbide. The methods and kits of the present invention are particularly useful for isolating RNA and DNA molecules having a desired minimum size during the preparation of a sequencing library.

BACKGROUND

For many applications in molecular biology, and particularly applications in global gene expression analysis, it is often necessary to separate desired nucleic acid sequences from other non-desired sequences. Often, this separation is based on size differences in the nucleic acids. One such global gene expression analysis application—wherein smaller undesired nucleic acids must be separated from larger, desired nucleic acids—is in massive parallel sequencing, also known as next generation sequencing. Next generation sequencing (NGS) involves the sequencing of a large number of reads (as much as over 40 billion) per instrument run.

There are many different platforms that can be used for next generation sequencing, including Roche 454, Roche GS FLX Titanium, Illumina MiSeq, Illumina HiSeq, Illumina Genome Analyzer IIX, Life Technologies SOLiD4, Life Technologies Ion Proton, Complete Genomics, Helicos Biosciences Heliscope, and Pacific Biosciences SMRT. All of the different platforms for next generation sequencing follow the same general procedure, namely preparing the purified RNA or DNA into a sequencing library, followed by massive parallel sequencing of relatively short sequences and subsequent bioinformatics to de-multiplex samples, align, annotate and aggregate reads, among other things.

In order to generate a sequencing library, multiple enzymatic reactions are required to modify and/or amplify the original input nucleic acid (RNA or DNA). In particular, fragments of nucleic acids, usually in the form of RNA or DNA oligonucleotides, are added to both the 5' and 3' end of the template nucleic acid targeted for sequencing. The best quality libraries will ensure that all the resulting reads obtained are dedicated to the targeted RNA or DNA template. However, in many cases, the usable read number is drastically reduced due to various contaminants being incorporated into the library, including adapter monomers as well as adapter-adapter ligation products. In addition, as these contaminants are of nucleic acid-origin, their presence in the final library preparation could negatively affect the accuracy of library quantification and the subsequent amount of library loaded onto the sequencing platform.

Different purification technologies have been utilized to tackle the issue of removing unligated adapter monomers and adapter-adapter ligation products from NGS libraries. Some methods are directed at removing the excessive adapters prior to cDNA synthesis and PCR amplification, while others are directed at purifying the desired library containing the inserts of interest for sequencing from gels based on size. However, all of these current methods have shortcomings. For example, gel purification usually requires a lengthy workflow and subsequent purification and will add an extensive amount of time to the library preparation (sometimes overnight). In addition, most of the existing purification systems may not be able to resolve small size differences at the low nucleic acid molecular weight range (such as in the case of small RNA sequence ligation steps).

SUMMARY OF INVENTION

Disclosed are methods and kits suitable for the size selective isolation of nucleic acids using silicon carbide.

In one aspect, disclosed is a method for isolating nucleic acids having a size above a desired cut-off size from a nucleic acid containing sample, comprising the steps of:
 a) combining the sample with a binding buffer, alcohol and silicon carbide to provide a binding mixture, wherein the nucleic acids having a size above the cut-off size bind to the silicon carbide, and wherein the cut-off size is determined by the alcohol concentration of the binding mixture;
 b) separating the bound nucleic acids from the remaining sample;
 c) optionally, washing the bound nucleic acids; and
 d) eluting the bound nucleic acids from the silicon carbide.

This size selective isolation method can be employed in a variety of applications, and in particular, the preparation of sequencing libraries, such as next generation sequencing libraries.

In one embodiment of the disclosed size selective isolation method, the alcohol is ethanol, isopropanol or methanol.

In another embodiment, the alcohol is ethanol and the ethanol concentration of the binding buffer and/or the binding mixture is at least about 10% (v/v) and the cut-off size is about 43 nucleotides or larger. In a further embodiment, the ethanol concentration of the binding buffer and/or the binding mixture is at least about 25% (v/v) and the cut-off size is about 22 nucleotides or larger. In a still further embodiment, the ethanol concentration of the binding buffer and/or the binding mixture is at least about 50% (v/v) and the cut-off size is about 10 nucleotides or larger.

In another embodiment, the silicon carbide can be provided in a column, such as a spin column. In a further embodiment, the silicon carbide can be provided as slurry.

In another embodiment, the nucleic acid can be a single stranded RNA, a double stranded RNA, a single stranded DNA, a double stranded DNA or a double stranded RNA/DNA hybrid.

In another embodiment, the nucleic acid containing sample may comprise: i) extracted nucleic acids, which have optionally been subject to mechanical or enzymatic treatment; ii) amplification reaction products; and/or iii) ligation reaction products. In a further embodiment, the amplification reaction products can be polymerase chain reaction (PCR) products. In a still further embodiment, the ligation reaction products are adaptor ligation products, wherein the adaptor ligation products are nucleic acids flanked by 5' and/or 3' adapters; adapter monomers; and/or adapter-adapter ligation products In another embodiment, the nucleic acid containing sample is obtained during the preparation of a sequencing library. In a further embodiment, the nucleic acid containing sample is obtained during the preparation of a next generation sequencing library and the nucleic acid containing sample is an adapter ligation sample comprising nucleic acids flanked by 5' and/or 3' adapters; adapter monomers; and/or adapter-adapter ligation products.

In another embodiment, the method can be used for isolating adapter-ligated RNA molecules from an adapter ligation sample and for removing adapter monomers and adapter-adapter ligation products based on the larger size of the adapter-ligated RNA molecules, and wherein step a) comprises contacting the adapter ligation sample with the binding buffer, alcohol and silicon carbide and binding adapter ligated RNA molecules to the silicon carbide, wherein under the used alcohol concentration, the adapter monomers and adapter-adapter ligation products substantially do not bind to the silicon carbide. In a further embodiment, the cut-off size lies above the size of adapter monomers and above the size of expected adapter-adapter ligation products and wherein the cut-off size is at least 10 nucleotides, at least 15 nucleotides, at least 20 nucleotides, at least 25 nucleotides or at least 30 nucleotides above the size of expected adapter-adapter ligation products.

In another aspect, disclosed is a method for preparing a small RNA library suitable for next generation sequencing, wherein said method comprises:
  a) isolating small RNA molecules from a sample;
  b) performing a 3' adapter ligation step to provide a 3' adaptor ligation reaction mixture comprising single stranded small RNA molecules that are flanked 3' by adapters;
  c) isolating single stranded small RNA molecules having a fragment size above a predetermined cut-off size in order to remove 3' adapter monomers and adapter-adapter ligation products, wherein said size selection step comprises:
    i) combining the 3' adaptor ligation reaction mixture with a binding buffer, alcohol and silicon carbide to provide a binding mixture, wherein the single stranded small RNA molecules having a fragment size above the cut-off size bind to the silicon carbide, and wherein the cut-off size is determined by the alcohol concentration of the binding mixture;
    ii) separating the bound single stranded small RNA molecules from the remaining ligation reaction mixture;
    iii) optionally, washing the bound single stranded small RNA molecules; and
    iv) eluting the bound single stranded small RNA molecules from the silicon carbide;
  d) performing a 5' adapter ligation step to provide a 5' adaptor ligation reaction mixture comprising single stranded small RNA molecules that are flanked 3' and 5' by adapters;
  e) optionally, performing a step of isolating single stranded small RNA molecules having a fragment size above a predetermined cut-off size in order to remove 5' adapter monomers and adapter-adapter ligation products, wherein said size selection step comprises:
    i) combining the 5' adaptor ligation reaction mixture with a binding buffer, alcohol and silicon carbide to provide a binding mixture, wherein the single stranded small RNA molecules having a fragment size above the cut-off size bind to the silicon carbide, and wherein the cut-off size is determined by the alcohol concentration of the binding mixture;
    ii) separating the bound single stranded small RNA molecules from the remaining ligation reaction mixture;
    iii) optionally, washing the bound single stranded small RNA molecules; and
    iv) eluting the bound single stranded small RNA molecules from the silicon carbide;
  f) reverse transcribing single stranded RNA molecules flanked with 5' and 3' adaptors to provide single stranded cDNA molecules; and
  g) amplifying the single stranded cDNA molecules by limited cycle PCR to incorporate an index sequence.

In one embodiment of the disclosed methods for preparing a small RNA library suitable for next generation sequencing, the alcohol is ethanol, isopropanol or methanol.

In another embodiment, the alcohol is ethanol and the ethanol concentration of the binding buffer and/or the binding mixture is at least about 10% (v/v) and the cut-off size is about 43 nucleotides or larger. In a further embodiment, the ethanol concentration of the binding buffer and/or the binding mixture is at least about 25% (v/v) and the cut-off size is about 22 nucleotides or larger. In a still further embodiment, the ethanol concentration of the binding buffer and/or the binding mixture is at least about 50% (v/v) and the cut-off size is about 10 nucleotides or larger.

In another embodiment, the silicon carbide can be provided in a column, such as a spin column. In a further embodiment, the silicon carbide can be provided as slurry.

In another aspect, disclosed is a method for preparing a small RNA library suitable for next generation sequencing, wherein said method comprises:
  a) isolating small RNA molecules from a sample;
  b) performing a 5' adapter ligation step to provide a 5' adaptor ligation reaction mixture comprising single stranded small RNA molecules that are flanked 5' by adapters;
  c) isolating single stranded small RNA molecules having a fragment size above a predetermined cut-off size in order to remove 5' adapter monomers and adapter-adapter ligation products, wherein said size selection step comprises:
    i) combining the 5' adaptor ligation reaction mixture with a binding buffer, alcohol and silicon carbide to provide a binding mixture, wherein the single stranded small RNA molecules having a fragment size above the cut-off size bind to the silicon carbide, and wherein the cut-off size is determined by the alcohol concentration of the binding mixture;
    ii) separating the bound single stranded small RNA molecules from the remaining ligation reaction mixture;
    iii) optionally, washing the bound single stranded small RNA molecules; and
    iv) eluting the bound single stranded small RNA molecules from the silicon carbide;
  d) performing a 3' adapter ligation step to provide a 3' adaptor ligation reaction mixture comprising single stranded small RNA molecules that are flanked 3' and 5' by adapters;
  e) optionally, performing a step of isolating single stranded small RNA molecules having a fragment size above a predetermined cut-off size in order to remove 3' adapter monomers and adapter-adapter ligation products, wherein said size selection step comprises:
    i) combining the 3' adaptor ligation reaction mixture with a binding buffer, alcohol and silicon carbide to provide a binding mixture, wherein the single stranded small RNA molecules having a fragment size above the cut-off size bind to the silicon carbide, and wherein the cut-off size is determined by the alcohol concentration of the binding mixture;

ii) separating the bound single stranded small RNA molecules from the remaining ligation reaction mixture;

iii) optionally, washing the bound single stranded small RNA molecules; and iv) eluting the bound single stranded small RNA molecules from the silicon carbide;

f) reverse transcribing single stranded RNA molecules flanked with 5' and 3' adaptors to provide single stranded cDNA molecules; and g) amplifying the single stranded cDNA molecules by limited cycle PCR to incorporate an index sequence.

In one embodiment of the disclosed method for preparing a small RNA library suitable for next generation sequencing, the alcohol is ethanol, isopropanol or methanol.

In another embodiment, the alcohol is ethanol and the ethanol concentration of the binding buffer and/or the binding mixture is at least about 10% (v/v) and the cut-off size is about 43 nucleotides or larger. In a further embodiment, the ethanol concentration of the binding buffer and/or the binding mixture is at least about 25% (v/v) and the cut-off size is about 22 nucleotides or larger. In a still further embodiment, the ethanol concentration of the binding buffer and/or the binding mixture is at least about 50% (v/v) and the cut-off size is about 10 nucleotides or larger.

In another embodiment, the silicon carbide can be provided in a column, such as a spin column. In a further embodiment, the silicon carbide can be provided as slurry.

In another aspect, disclosed is a kit for the selective binding of nucleic acids having a size above a desired cut-off size, comprising: a) a binding buffer to be combined with ethanol to provide an ethanol concentration of about 1 to about 50% (v/v); b) a wash solution; c) an elution solution; d) silicon carbide, and e) instructions for adjusting the ethanol concentration to selectively bind nucleic acids having a size above the desired cut-off size; wherein the cut-off size is at least about 10 nucleotides.

In one embodiment, the silicon carbide can be provided in a column, such as a spin column. In a further embodiment, the silicon carbide can be provided as slurry.

In another embodiment, the ethanol concentration is at least about 10% (v/v) and the cut-off size is about 43 nucleotides or larger. In a further embodiment, the ethanol concentration is at least about 25% (v/v) and the cut-off size is about 22 nucleotides or larger. In a still further embodiment, the ethanol concentration is about 50% (v/v) and the cut-off size is about 10 nucleotides or larger.

BRIEF DESCRIPTION OF THE DRAWINGS

FIG. 6, panel B is a Venn diagram generated using miRNA with reads equal or more than 5 RPM (reads per millions) and which illustrates that both the blocking oligonucleotide and SiC based size exclusion cleanup methods shared the same diversity of 200 microRNAs and with the SiC based size exclusion method yielding more unique miRNAs.

DESCRIPTION

Figure 1:
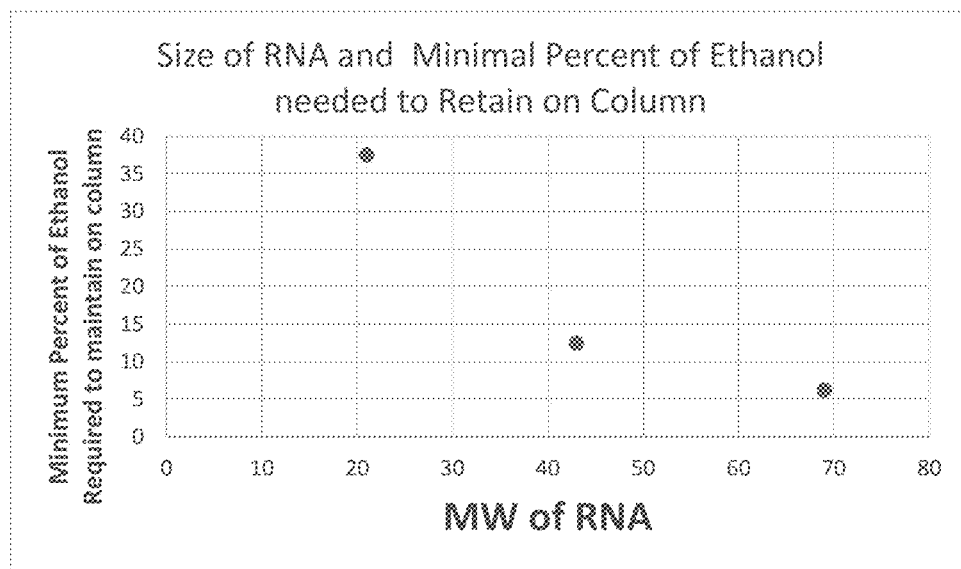
FIG. 1 is a graph comparing the size of RNA molecules captured by a SiC column using different binding buffers having varying concentrations of ethanol.

It has been unexpectedly found that the size of nucleic acids bound to silicon carbide (SiC) can be controlled by the alcohol concentration used during the binding step. This finding allows for size selective binding of nucleic acids, and in particular, small nucleic acids such as microRNAs (miRNAs), from a sample containing different sized nucleic acids. The cut-off size (e.g. the minimum desired size) for the targeted nucleic acids can be set by selecting the appropriate alcohol concentration for the binding step. Generally, the higher the concentration of alcohol used during the binding step, the lower the cut-off size of the nucleic acids that will be selectively bound to the SiC. Size selective binding of nucleic acids to SiC can be used in various applications, including as part of a cleanup step in the preparation of sequencing libraries. It has been further surprisingly found that use of a SiC based cleanup step in the preparation of a small RNA sequencing library may enhance the number of different miRNA incorporated into the sequencing library as compared to prior art cleanup methods.

Method for Isolating Nucleic Acids Based on Size

Disclosed is a method for isolating nucleic acids having a size above a desired cut-off size from a nucleic acid containing sample. The method comprises the steps of:

a) combining the sample with a binding buffer, alcohol and SiC to provide a binding mixture, wherein nucleic acids having a size above the desired cut-off size are selectively bound to the SiC and wherein the cut-off size for selective binding to the SiC is determined by the alcohol concentration of the binding mixture;

b) separating the bound nucleic acids from the remaining sample;

c) optionally, washing the bound nucleic acids; and d) eluting the bound nucleic acids from the SiC.

As used herein, "size" refers to the length of the nucleic acid, expressed either in terms of the number of nucleotides (nt) or the number of base pairs (bp) in the context of double stranded nucleic acids. The "desired cut-off size" refers to the minimum size of the target nucleic acids to be isolated. For example, if the targeted nucleic acids are those having a length >100 nt, then the "desired cut-off size" would be 100 nt and the concentration of alcohol adjusted accordingly to affect selective binding of those nucleic acids having a length >100 nt.

The disclosed size selective isolation method can be used to selectively enrich the population of target nucleic acids that are the desired minimum size and/or selectively deplete the population of non-target nucleic acids that are shorter than the desired minimum size. This is accomplished by selecting the appropriate alcohol concentration for the binding step, as the alcohol concentration determines the cut-off size for the nucleic acids that will selectively bind to the SiC. Nucleic acids having a size above the cut-off size will efficiently bind to the SiC, while nucleic acids having a size below the cut-off size are predominantly not bound and are not recovered by the SiC. Therefore, nucleic acids shorter than the cut-off size are efficiently depleted and nucleic acid molecules having the desired minimum size are enriched.

In a preferred embodiment, the disclosed size selective isolation method can be used specifically to isolate adapter-ligated RNA molecules from an adapter ligation sample and to remove adapter monomers and adapter-adapter ligation products based on the larger size of the adapter-ligated RNA molecules, wherein step a) comprises contacting the adapter ligation sample with the binding buffer, alcohol and silicon carbide and binding adapter ligated RNA molecules to the silicon carbide, wherein under the used alcohol concentration, the adapter monomers and adapter-adapter ligation products substantially do not bind to the binding matrix. In this preferred embodiment, the cut-off size lies above the size of adapter monomers and above the size of expected adapter-adapter ligation products. Preferably, the cut-off size is at least 10 nt, at least 15 nt, at least 20 nt, at least 25 nt or at least 30 nt above the size of expected adapter-adapter ligation products.

The removal of undesirable small nucleic acids achieved with the disclosed size selective isolation method does not need to be a complete removal. For various applications, including applications associated with library preparation for next generation sequencing, it is sufficient to deplete small nucleic acid molecules to an extent such that their interference with downstream applications, such as sequencing, is reduced. As will be described in greater detail below, it is not necessary that 100% of the small nucleic acids are removed during utilization of the disclosed size selective isolation method in the preparation of sequencing libraries.

Nucleic Acid Containing Samples

The nucleic acid containing sample may comprise different types of nucleic acids and nucleic acids of different sizes (i.e. lengths). The nucleic acid containing sample may comprise single stranded RNA, double stranded RNA, single stranded DNA, double stranded DNA, and/or a double stranded RNA/DNA hybrid. Preferably, the nucleic acids are single stranded RNA or double stranded RNA/DNA hybrids.

The nucleic acid containing sample can be of various origins, including biological samples and artificial samples. The nucleic acid containing sample may comprise extracted nucleic acids (e.g. from nucleic acids derived from cells, tissues, bodily fluids) or synthetic nucleic acids. The extracted or synthetic nucleic acids can be further processed by way of various mechanical (e.g. shearing) and enzymatic treatments (e.g. treatment with a proteinase, lipases, DNase, RNase as appropriate).

The nucleic acid containing sample may comprise nucleic acids obtained after an enzymatic reaction, including but not limited to amplification reactions, ligation reactions, and in particular, adapter ligation reactions. The nucleic acid containing sample may comprise amplification products (e.g. PCR products) and/or adaptor ligation products (e.g. nucleic acids flanked by 5' and/or 3' adapters; adapter monomers; adapter-adapter ligation products).

The nucleic acid containing sample can be obtained during the preparation of a sequencing library, in particular, during the preparation of a next generation sequencing (NGS) library. According to one preferred embodiment, the nucleic acid containing sample is an adapter ligation sample obtained as a result of an adapter ligation step during library preparation for next generation sequencing. The sample may comprise (i) single stranded RNA molecules that are ligated to 5' and/or 3' adapters, (ii) adapter monomers and (iii) adapter-adapter ligation products including adapter dimers.

Size Selective Binding

In one embodiment, the nucleic acid containing sample can be combined with a binding buffer, an alcohol and SiC slurry to provide a binding mixture. The SiC slurry can be prepared with a typical industrial preparation of SiC, which is composed of about 97.8% silicon carbide and small amounts of silicon dioxide, silicon, iron, aluminum and carbon. SiC is available in a variety of grit sizes or grades, with each grade having a different average particle size. The SiC slurry can be prepared using any grade of SiC and an appropriate liquid carrier, such as PBS buffers (e.g. 1×PBS, pH 7) and Tris buffers (e.g. 10 mM Tris, pH 7). The SiC can have a grit size between 500-2500 (diameter ca. 1-10 μm), preferably a grit size between 2000-2500 and even more preferably, a grit size of 2500. The SiC slurry can be prepared in various ratios of SiC to liquid carrier, with a preferred ratio being between 30% and 70% (w/v), and even more preferred ratio being 50% (w/v).

In order to isolate nucleic acids having a size above the desired cut-off size from the nucleic acid containing sample, the alcohol concentration of the binding mixture needs to be adjusted to the appropriate concentration. The alcohol concentration used will depend on the desired cut-off size for the target nucleic acid and the alcohol used.

The alcohol concentration in the binding mixture can be adjusted using any alcohol known in the art. Examples of suitable alcohols include are but not limited to ethanol, isopropanol and methanol. To achieve size selective binding of the target size nucleic acids to the SiC, the alcohol concentration of the binding mixture can be adjusted to a concentration of between 1-50% (v/v), more preferably between 10-40% (v/v), and even more preferably between 20-30% (v/v) depending on the desired cut-off size. The appropriate alcohol concentration can be easily determined by titrating the alcohol concentration. It will be appreciated that one only needs to determine the minimum alcohol concentration necessary for preferential SiC binding of the target size nucleic acids (e.g. the amount of bound target size nucleic acids is greater than the amount of bound non-target size nucleic acids), as downstream applications, such as sequencing, do not require the complete removal of non-target size nucleic acids.

As shown in FIG. 1, when ethanol is used to adjust the alcohol concentration of the binding mixture, the use of a minimum ethanol concentration of about 6% (v/v) can provide a cut-off size of about 69 nt. Use of a minimum ethanol concentration of about 13% (v/v) can provide a cut-off size of about 43 nt. Use of a minimum ethanol concentration of about 38% (v/v) can provide a cut-off size of about 21 nt.

In general, ethanol concentrations of at least 10% (v/v) can be used to selectively bind nucleic acids that are 43 nt and larger; ethanol concentrations of at least 25% (v/v) can be used to selectively bind nucleic acids that are 22 nt and larger; and ethanol concentrations of at least 50% (v/v) can be used to selectively bind nucleic acids that are 10 nt and larger.

Figure 2:
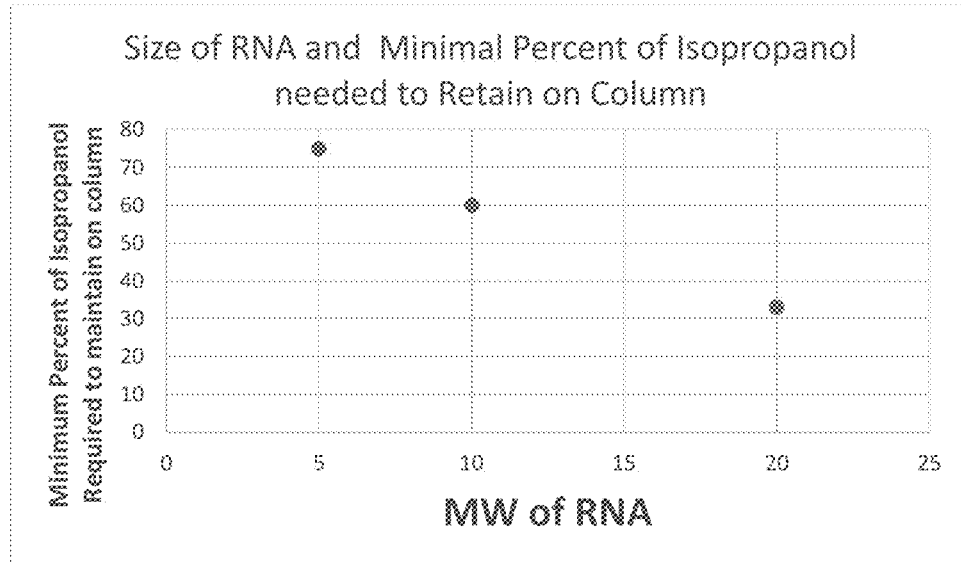
FIG. 2 is a graph comparing the size of RNA molecules captured by a SiC column using different binding buffers having varying concentrations of isopropanol.

As shown in FIG. 2, isopropanol can be preferably used for selectively removing very small nucleic acids. Use of a minimum isopropanol concentration of about 33% (v/v) can provide a cut-off size of about 20 nt. Use of a minimum isopropanol concentration of about 60% (v/v) can provide a cut-off size of about 10 nt. Use of a minimum isopropanol concentration of about 75% (v/v) can provide a cut-off size of about 5 nt.

In general, isopropanol concentrations of at least 10% (v/v) can be used to selectively bind nucleic acids that are 20 nt and larger; isopropanol concentrations of at least 25% (v/v) can be used to selectively bind nucleic acids that are 10 nt and larger; and isopropanol concentrations of at least 50% (v/v) can be used to selectively bind nucleic acids that are 5 nt and larger.

The appropriate amount of alcohol (e.g. the amount which will yield the desired alcohol concentration in the binding mixture) can be added to the binding buffer and the sample prior to combining the binding buffer and the sample with the SiC slurry to provide the binding mixture. Alternatively, the alcohol concentration can be adjusted to the appropriate concentration after the binding buffer, sample and the SiC slurry have been combined together to provide the binding mixture.

The size selective binding step can be performed under low salt conditions and slightly acidic to neutral pH conditions of about pH 4-7. The nucleic acids contained in the sample having a size above the desired cut-off size will come into contact to with the SiC and selectively bind to the SiC particles. The SiC particles with the bound nucleic acids can then be separated from the liquid phase (which contains the smaller unbound nucleic acids) through pelleting by centrifugation, or by passing the SiC particles through a solid support column or through gravity settling. Once the bound SiC particles have been separated, the size selected nucleic acids can optionally be washed with an appropriate low salt wash solution (for example, 1-100 mM Tris.HCl, MOPS or HEPES with 0-100 mM NaCl or KCl) to remove materials not selectively bound to the solid support. The bound size selected nucleic acids can then be eluted using an appropriate low salt elution solution (for example, 1-10 mM Tris.HCl or water) under slightly basic to neutral pH conditions of about pH 7-9 and collected for downstream applications.

In another embodiment of the method, the SiC can be used in a column format. The term "column" as used herein describes a container having at least two openings. Thereby, a solution and/or sample can pass through said column. A SiC slurry as described above, can be packed into a column of any size, from small spin columns all the way to large chromatography columns operating through the use of gravity or pumps. The choice of column size will depend on the volume of the nucleic acid containing sample to be processed.

For embodiments employing a SiC column, the alcohol concentration can be adjusted to the appropriate concentration using any alcohol as described above. For example, the appropriate amount of alcohol can be added to the binding buffer and the sample. The resulting combination of the binding buffer, the alcohol and the sample can then be introduced into the SiC column to provide the binding mixture.

For example, a nucleic acid containing sample can be mixed with a suitable amount of a low salt binding buffer having a slightly acidic to neutral pH of about pH 4-7, the appropriate amount of alcohol can be added and the resulting mixture can be loaded into a spin column using a pipette. The spin column is centrifuged causing the sample to travel through the spin column. The nucleic acids contained in the sample having a size above the desired cut off size will come into contact with the SiC and selectively bind to the SiC, while any nucleic acids below the desired cut-off size will be removed in the flowthrough. The size selected bound nucleic acids can be optionally washed with an appropriate low salt wash solution (for example, 1-100 mM Tris.HCl, MOPS or HEPES with 0-100 mM NaCl or KCl) to remove materials not selectively bound to the solid support. The size selected bound nucleic acids can then be eluted from the SiC by passing an appropriate low salt elution solution (for example, 1-10 mM Tris.HCl or water) under slightly basic to neutral pH conditions of about pH 7-9, and the eluted nucleic acids can be collected for downstream applications.

Preparation of Sequencing Libraries

The disclosed size selective isolation method is particularly suited for performing size selection steps (e.g. removal of non-target nucleic acids and contaminants) during the preparation of a sequencing library for next generation sequencing. The disclosed isolation method can be integrated into existing work-flows for preparing next generation sequencing libraries, in particular, small RNA libraries, wherein adapter ligation steps are usually performed in the early stages of library preparation.

Through the application of the disclosed size selective isolation method during library preparation, the library preparation process can be greatly improved by eliminating the lengthy procedure of having to gel purify the library prior to sequencing in order to remove adapter monomers and adapter-adapter ligation products. Prior art gel purification steps typically take 1 day to perform, whereas use of the disclosed size selective isolation method for cleaning up adapter monomers and adapter-adapter ligation products during library preparation may take less than 1 hour.

To prepare a small RNA library for next generation sequencing, adapters are ligated to the 5' and/or 3' ends of single stranded RNA fragments. The specific design of the adapters will depend on the next generation sequencing platform to be used, and for the purposes of this discussion, any adaptors useful for preparing sequencing libraries for next generation sequencing can be used. The adapter sequences provide a known sequence composition allowing for annealing of primers for cDNA generation, as well as for amplification and addition of an index during subsequent steps of library preparation.

For efficient adapter ligation during library preparation, the adapters are usually used in excess during the adapter ligation step. Typically, during small RNA library preparation for next generation sequencing, the 3' adapter is ligated first. Therefore, excess amounts of the adapter are added to the purified small RNA in order to ensure that all small RNA molecules present will bind to an adapter. Thus, after 3' adapter ligation an RNA containing sample is provided which comprises RNA molecules that are ligated at the 3' end to an adapter, as well as unligated adapter monomers and adapter-adapter ligation products including adapter dimers. At the next step in the library preparation, the 5' adapter is then ligated to the small RNA molecules, which already have a ligated 3' adapter. Again, excess amounts of the 5' adapter are added to ensure that all the RNA molecules will be flanked by both a 3' and a 5' adapter.

A problem with conventional library preparation methods lies in the fact that the 5' adapter can ligate to the 3' adapter monomers, thereby resulting in ligation products that can become incorporated into that library and that will diminish the sequencing power of the subsequent sequencing reaction. Therefore, these unligated adapter monomers and adapter-adapter products should be removed before starting the sequencing run.

Common prior art clean up methods for removing of library contaminants (e.g. PEG/bead based methods, gel based purifications) can be time consuming and labour intensive. Furthermore, the majority of the prior art methods are performed as the last step before starting the sequencing of the small RNA library, as such, the formation of 5' adapter-3' adapter ligated products are not avoided. These problems are avoided by incorporating the disclosed size selective isolation method into the library preparation method.

In contrast to the prior art library preparation methods, the disclosed method for preparing a small RNA library suitable for next generation sequencing quickly removes library contaminants (e.g. 1 day for gel based purification vs. about 1 hour for the disclosed size selective isolation method). Further in contrast to prior art methods, the disclosed method for preparing a small RNA library suitable for next generation sequencing comprises a size based cleanup step that is performed after the first 3' adapter ligation in a small RNA sequencing library preparation process rather than as an end step in the library preparation. By employing a size selective isolation step early on in the preparation of the library, it is possible to avoid and/or reduce the formation of 5' adapter-3' adapter ligated products. The size based cleanup step allows for the removal of excess unligated 3' adapters and reduces the likelihood of the formation of 5' adapter-3' adapter ligated products without any RNA insert.

It will be apparent to those skilled in the art that the size selective isolation cleanup step can also be performed after the 5' adapter ligation step as well. Furthermore, it will be apparent to those skilled in the art that the method can also be used for size selective RNA isolation when the 5' adapter is ligated to the RNA prior to the 3' adapter, and again the size selective RNA isolation can be performed after the 5' adaptor ligation and/or after the subsequent 3' adapter ligation.

In a preferred embodiment, disclosed is a method for preparing a small RNA library suitable for next generation sequencing, the method comprising the steps of:
a) isolating small RNA molecules from a sample;
b) performing a 3' adapter ligation step to provide a 3' adaptor ligation reaction mixture comprising single stranded small RNA molecules that are flanked 3' by adapters;
c) isolating single stranded small RNA molecules having a fragment size above a predetermined cut-off size in order to remove 3' adapter monomers and adapter-adapter ligation products, wherein said size selection step comprises:
   i) combining the 3' adaptor ligation reaction mixture with a binding buffer, alcohol and silicon carbide to provide a binding mixture, wherein the single stranded small RNA molecules having a fragment size above the cut-off size bind to the silicon carbide, and wherein the cut-off size is determined by the alcohol concentration of the binding mixture;
   ii) separating the bound single stranded small RNA molecules from the remaining ligation reaction mixture;
   iii) optionally, washing the bound single stranded small RNA molecules; and
   iv) eluting the bound single stranded small RNA molecules from the silicon carbide;
d) performing a 5' adapter ligation step to provide a 5' adaptor ligation reaction mixture comprising single stranded small RNA molecules that are flanked 3' and 5' by adapters;
e) optionally, performing a step of isolating single stranded small RNA molecules having a fragment size above a predetermined cut-off size in order to remove 5' adapter monomers and adapter-adapter ligation products, wherein said size selection step comprises:
   i) combining the 5' adaptor ligation reaction mixture with a binding buffer, alcohol and silicon carbide to provide a binding mixture, wherein the single stranded small RNA molecules having a fragment size above the cut-off size bind to the silicon carbide, and wherein the cut-off size is determined by the alcohol concentration of the binding mixture;
   ii) separating the bound single stranded small RNA molecules from the remaining ligation reaction mixture;
   iii) optionally, washing the bound single stranded small RNA molecules; and
   iv) eluting the bound single stranded small RNA molecules from the silicon carbide;
f) reverse transcribing single stranded RNA molecules flanked with 5' and 3' adaptors to provide single stranded cDNA molecules; and
g) amplifying the single stranded cDNA molecules by limited cycle PCR to incorporate an index sequence.

The size selection steps can be performed using either a SiC slurry or a SiC column as described in greater detail above.

In another preferred embodiment, disclosed is a method for preparing a small RNA library suitable for next generation sequencing, wherein said method comprises:
a) isolating small RNA molecules from a sample;
b) performing a 5' adapter ligation step to provide a 5' adaptor ligation reaction mixture comprising single stranded small RNA molecules that are flanked 5' by adapters;
c) isolating single stranded small RNA molecules having a fragment size above a predetermined cut-off size in order to remove 5' adapter monomers and adapter-adapter ligation products, wherein said size selection step comprises:
   i) combining the 5' adaptor ligation reaction mixture with a binding buffer, alcohol and silicon carbide to provide a binding mixture, wherein the single stranded small RNA molecules having a fragment size above the cut-off size bind to the silicon carbide, and wherein the cut-off size is determined by the alcohol concentration of the binding mixture;
   ii) separating the bound single stranded small RNA molecules from the remaining ligation reaction mixture;
   iii) optionally, washing the bound single stranded small RNA molecules; and
   iv) eluting the bound single stranded small RNA molecules from the silicon carbide;
d) performing a 3' adapter ligation step to provide a 3' adaptor ligation reaction mixture comprising single stranded small RNA molecules that are flanked 3' and 5' by adapters;
e) optionally, performing a step of isolating single stranded small RNA molecules having a fragment size above a predetermined cut-off size in order to remove 3' adapter monomers and adapter-adapter ligation products, wherein said size selection step comprises:
   i) combining the 3' adaptor ligation reaction mixture with a binding buffer, alcohol and silicon carbide to provide a binding mixture, wherein the single stranded small RNA molecules having a fragment size above the cut-off size bind to the silicon carbide, and wherein the cut-off size is determined by the alcohol concentration of the binding mixture;

ii) separating the bound single stranded small RNA molecules from the remaining ligation reaction mixture;

iii) optionally, washing the bound single stranded small RNA molecules; and iv) eluting the bound single stranded small RNA molecules from the silicon carbide;

f) reverse transcribing single stranded RNA molecules flanked with 5' and 3' adaptors to provide single stranded cDNA molecules; and g) amplifying the single stranded cDNA molecules by limited cycle PCR to incorporate an index sequence.

The size selection steps can be performed using either a SiC slurry or a SiC column as described in greater detail above.

Kits for the Selective Binding of Nucleic Acids

In a further embodiment, provided are kits for the selective binding of nucleic acid molecules having a size above a desired cut-off size, comprising: a) a binding buffer to be combined with an alcohol, preferably ethanol, to provide an alcohol concentration of about 1 to about 50% (v/v); b) SiC, c) a wash solution; and d) an elution solution, wherein the cut-off size is at least 5 nucleotides.

The kit can be provided with printed instructions that describe the appropriate amount of alcohol to be added to the binding buffer, sample and SiC to achieve the appropriate alcohol concentration in the binding mixture to affect selective binding of nucleic acids above the desired cut-off size. The SiC can be provided in a slurry format or in a column format. Details regarding the SiC slurry or column, as well as details regarding the addition of the alcohol to the binding mixture to achieve a desired alcohol concentration for selective binding were described in detail above in conjunction with the isolation method.

In a preferred embodiment, the disclosed kits can be used for isolating adapter-ligated RNA molecules from an adapter ligation sample and for removing adapter monomers and adapter-adapter ligation products based on the larger size of the adapter-ligated RNA molecules for use in preparing a small RNA sequencing library.

Although the invention has been described with reference to illustrative embodiments, it is to be understood that the invention is not limited to these precise embodiments, and that various changes and modification are to be intended to be encompassed in the appended claims.

EXAMPLES

These examples are described for the purposes of illustration and are not intended to limit the scope of the invention.

Example 1—Separation of Adapter-microRNA Ligated Molecules from Adapter Monomers To mimic the steps during a small RNA library preparation, synthetic oligos containing Adapter-microRNA ligated molecules were designed. The example used was based on a C. elegans mircoRNA (cel-miR-39) (miRBase Accession: MI0000010) with the sequence of:

(SEQ ID NO: 1)
5' UCACCGGGUGUAAAUCAGCUUG 3'

The synthetic Adapter-microRNA ligated molecule was generated by adding the Illumina TruSeq 3' Adapter sequence (RA3)

(SEQ ID NO: 2)
5' TGGAATTCTCGGGTGCCAAGG 3' to the 3' end of cel-miR-39, resulting in a final product of (SEQ ID NO: 3)
5' UCACCGGGUGUAAAUCAGCUUGTGGAATTCTCGGGTGCCAAGG 3', mimicking the product after the 3' adapter ligation step in the small RNA sequencing library preparation. Different fluorophores were added to the aforementioned molecules (FAM for cel-miR-39-RA3 ligated product and Hex for RA3 monomer) for subsequent tracking and quantification.

Figure 3:
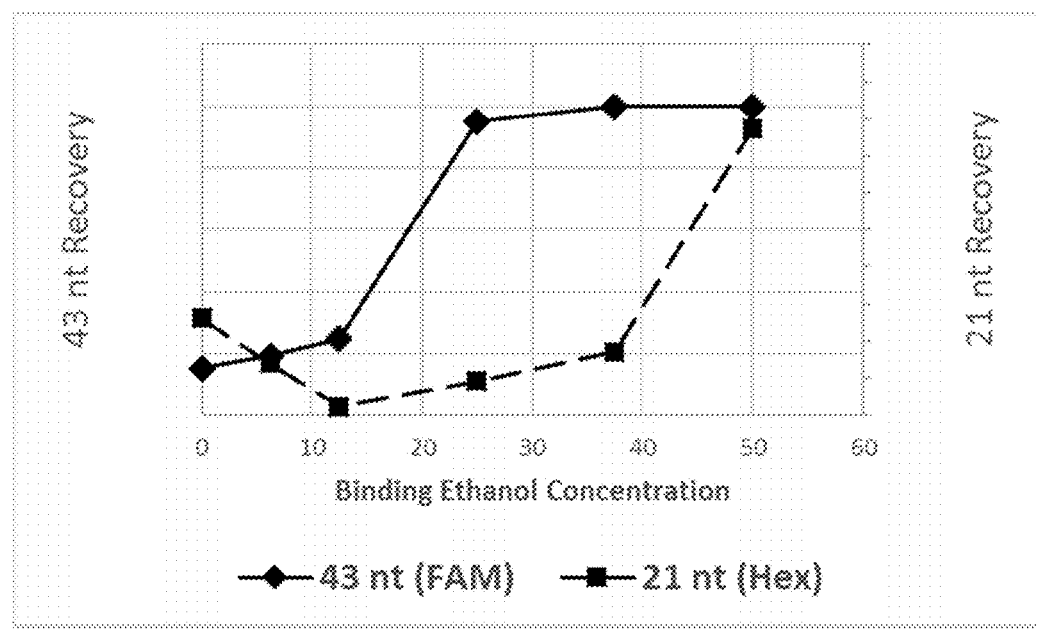
FIG. 3 is a line graph comparing the amount of FAM-cel-miR-39-RA3 (43 nt) and Hex-RA3 (21 nt) captured by a SiC column using different binding buffers having varying concentrations of ethanol.

In the example depicted in FIG. 3, each synthetic oligo (FAM-cel-miR-39-RA3 and Hex-RA3) was adjusted to a concentration of 1 μM and mixed at a 1:1 ratio. 20 μL of the mixture was then mixed with 180 μL of a Binding Solution (RNA Clean-Up and Concentration Micro-Elute Kit, Cat#61000, Norgen Thorold, Canada). The resulting mixture was adjusted to a final volume of 400 μL by adding various amounts of water and/or ethanol to give a final ethanol concentration of 0%, 6.25%, 12.5%, 25%, 37.5% and 50% (v/v). The oligo-ethanol mix was then applied to a spin column containing 5 mg SiC by centrifugation at 6,000 RPM (~3,500×g) for 1 minute. The column was washed twice with 600 μL of a Wash Solution (RNA Clean-Up and Concentration Micro-Elute Kit, Cat#61000, Norgen Thorold, Canada) by centrifugation at 14,000 RPM (~14,000×g) for 1 minute. The column was further dried by centrifugation at 14,000 RPM (~14,000×g) for 2 minutes. The RNA was then eluted with 10 μL of an Elution Solution (RNA Clean-Up and Concentration Micro-Elute Kit, Cat#61000, Norgen Thorold, Canada) by first centrifugation at 2,000 RPM (~200×g) for 1 minute, followed by centrifugation at 14,000 RPM (~14,000×g) for 2 minutes.

The presence of each synthetic oligo was then evaluated on a QIAGEN Rotor Gene Q (QIAGEN, Toronto, Canada) at the excitation and absorption wavelengths specific for FAM and Hex, respectively. As shown in FIG. 3, both cel-miR-39-RA3 (43 bp) and the RA3 (21 bp) were effectively captured by the column at ~50% (v/v) ethanol. However, as ethanol % (v/v) decreased, the amount of RA3 (21 bp) captured by the column drastically decreased, while a high amount of cel-miR-39-RA3 (43 bp) was still captured (data points of 25% (v/v) and 37.5% (v/v) ethanol), giving maximum separation. As ethanol % (v/v) further decreased, the cel-miR-39-RA3 captured by the column started to decrease but still maintained a higher level than RA3 at as little as ~10% (v/v) ethanol.

Example 2—Separation of microRNA Ligated at Both 5' and 3' Ends from Adapter Monomers To mimic the final modified RNA product during the library preparation, synthetic oligos containing microRNA with both 5' and 3' ends ligated with adapters were designed. The example used was based on a C. elegans mircoRNA (cel-miR-39) (miRBase Accession: MI0000010) with the sequence (SEQ ID NO: 1)
5' UCACCGGGUGUAAAUCAGCUUG 3'.

The synthetic 5'/3'-ligated molecule was generated by adding the Illumina TruSeq 3' Adapter sequence (RA3)

(SEQ ID NO: 2)
5' TGGAATTCTCGGGTGCCAAGG 3' to the 3' end of cel-miR-39 and Illumina TruSeq 5' Adapter sequence (RA5)

(SEQ ID NO: 4)
5' GUUCAGAGUUCUACAGUCCGACGAUC 3' to the 5' end of the same cel-miR-39 resulting in a final product of (SEQ ID NO: 5)
5'GUUCAGAGUUCUACAGUCCGACGAUCUCACCGGGUGUAAAUCAGCUU
GTGGAATTCTCGGGTGCCAAGG 3'.

Different fluorophores were added to the aforementioned molecules (Cy5.5 for RA5-cel-miR-39-RA3 ligated product and Hex for RA3 monomer) for subsequent tracking and quantification.

Figure 4:
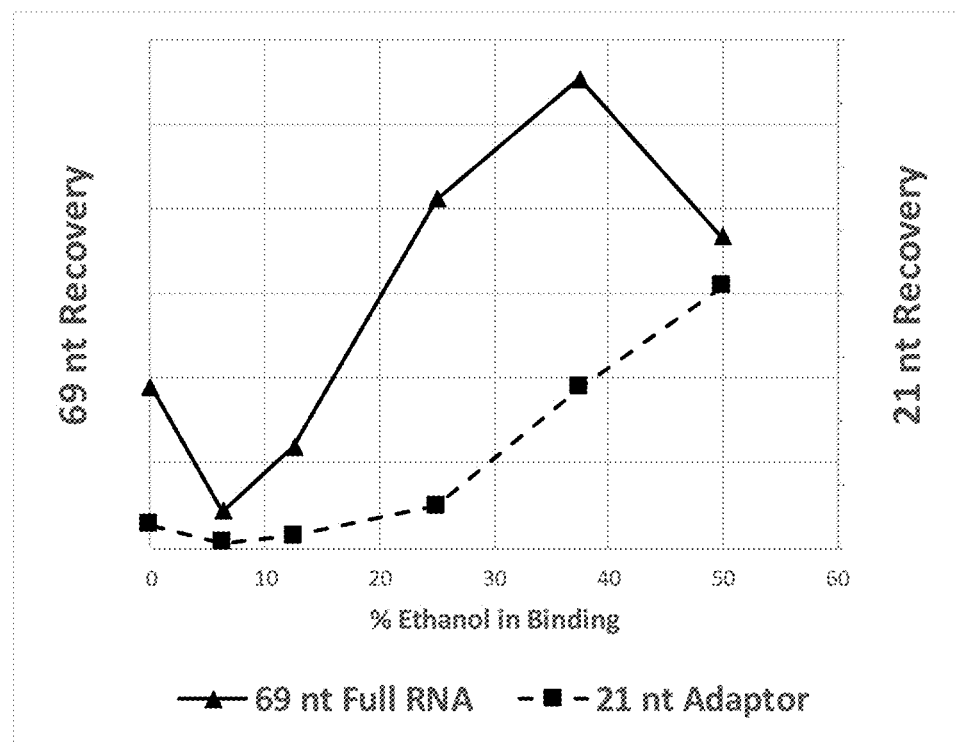
FIG. 4 is a line graph comparing the amount of RA5-cel-miR-39-RA3 (69 nt) and RA3 (21 nt) captured by a SiC column using different binding buffers having varying concentrations of ethanol.

In the example depicted in FIG. 4, each synthetic oligo (Cy5.5 for RA5-cel-miR-39-RA3 and Hex-RA3) was adjusted to a concentration of 1 µM and mixed at a 1:1 ratio. 20 µL of the mixture was then mixed with 180 µL of a Binding Solution (RNA Clean-Up and Concentration Micro-Elute Kit, Cat#61000, Norgen Thorold, Canada). The resulting mixture was adjusted to a final volume of 400 µL by adding various amounts of water and/or ethanol to give a final ethanol concentration of 0%, 6.25%, 12.5%, 25%, 37.5% and 50% (v/v). The oligo-ethanol mix was then applied to a spin column containing 5 mg of SiC by centrifugation at 6,000 RPM (~3,500×g) for 1 minute. The column was washed twice with 600 µL of a Wash Solution (RNA Clean-Up and Concentration Micro-Elute Kit, Cat#61000, Norgen Thorold, Canada) by centrifugation at 14,000 RPM (~14,000×g) for 1 minute. The column was further dried by centrifugation at 14,000 RPM (~14,000×g) for 2 minutes. The RNA was then eluted with 10 µL of an Elution Solution by first centrifugation at 2,000 RPM (~200×g) for 1 minute, followed by centrifugation at 14,000 RPM (~14,000×g) for 2 minutes.

The presence of each synthetic oligo was then evaluated on a Qiagen Rotor Gene Q at the excitation and absorption wavelengths specific for Cy5.5 and Hex, respectively. As shown in FIG. 4, both RA5-cel-miR-39-RA3 (69 bp) and the RA3 (21 bp) were effectively captured by the column at ~50% (v/v) ethanol. However, as ethanol % (v/v) decreased, the amount of RA3 (21 bp) captured by the column drastically decreased, while a high amount of cel-miR-39-RA3 (43 bp) was still captured (data points of 25% and 37.5% ethanol), giving maximum separation. As ethanol % (v/v) further decreased, the RA5cel-miR-39-RA3 captured by the column started to decrease but still maintained a higher level than RA3 at as little as ~10% (v/v) ethanol.

Example 3—Effect of 3' Adapter Cleanup on Final Small RNA-Sequence Library Product To test the effect of adapter cleanup on the subsequent small RNA-sequence library product, libraries were prepared using a standard small RNA library procedure with or without the use of the SiC-based size separation technology. About 1 µg of HeLa total RNA or ~10 ng of human plasma RNA was used as an input. The RNA was first ligated at the 3' end in a 20 µL reaction using T4 RNA Ligase 2 (deleted mutant, Cat# T4RL2T-100, MC Lab, San Francisco, United States) and a pre-adenylated RA3 adapter. The ligation reaction was then subjected to size separation as described in Example 1, using 25% (v/v) ethanol as final binding concentration. A control without separation/cleanup was performed in parallel. The purified product was then subjected to 5' adapter ligation using T4 RNase Ligase 1 (Cat# T4RL1-100, MC Lab, San Francisco, United States) and RA5 adapter. The final ligated product (RA5-microRNA-RA3) was then subjected to cDNA synthesis using a M-MLV reverse transcriptase (Norgen TruScript Reverse Transcriptase, Cat#54440, Norgen, Thorold, Canada) and reverse primer complementary to the RA3 sequence. This was followed by a limited (15) cycle PCR amplification to enrich the cDNA and also to attach the indexing (barcode) sequences. The indexed libraries were then subjected to PCR clean-up using Norgen's PCR Purification Kit (Norgen, Thorold, Canada) and resolved on an Agilent High Sensitivity DNA Chip (Cat#5067-4626, Agilent, Santa Clara, United States).

Figure 5:
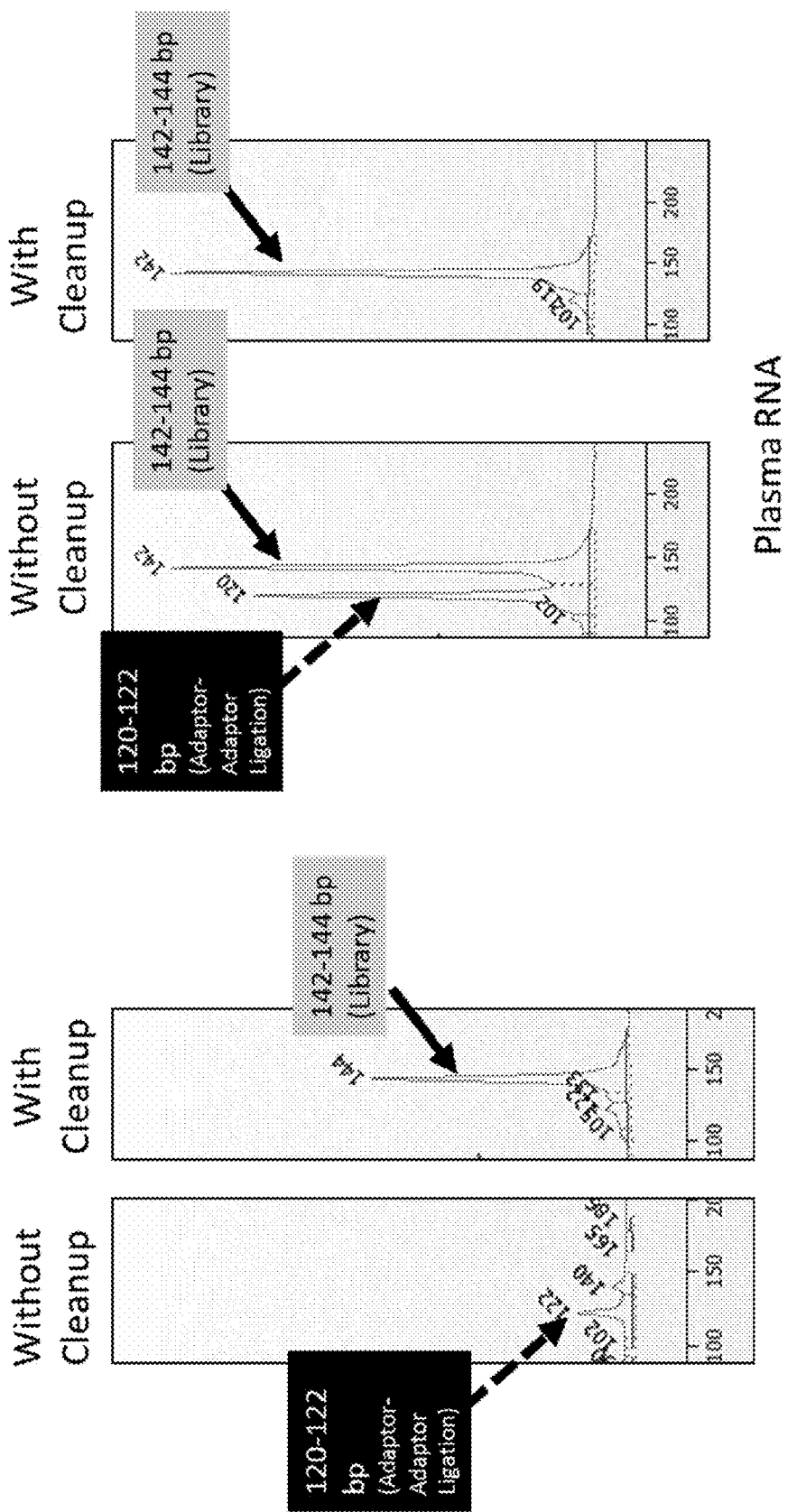
FIG. 5 compares the predominant PCR products obtained for HeLa RNA input (left panel) and for plasma RNA input (right panel), with and without adaptor cleanup prior to PCR amplification.

As shown in FIG. 5, without the 3' adapter cleanup removal, the predominant PCR product for HeLa RNA input was a 120-122 bp DNA, corresponding to product from 5' adapter-3' adapter ligation without any microRNA insert. Similarly, a 120-122 bp product was observed in the plasma RNA input product. In contrast, with the 3' adapter removal using SiC columns, a predominant PCR product of 142-144 bp was obtained, reflecting roughly a 20 bp difference, which is the size of the microRNA insert. This 142-144 bp PCR product was observed as the predominant product in both inputs, with little to no detection of the 120-122 bp product.

Example 4—Comparison of the Effect of 3' Adapter Cleanup Using an Established Blocking Oligo Method and the SiC-Based Column Removal Method on the Diversity of Small RNA-Sequence Library Products To test the effect of adapter cleanup on the miRNA diversity of the subsequent small RNA-sequence library product, libraries were prepared using a standard small RNA library procedure with the use of the SiC-based size separation technology for 3' adapter cleanup and compared to the use of a blocking oligonucleotide for 3' adapter cleanup (as illustrated in U.S. Pat. No. 8,883,421).

Approximately 10 ng of human plasma RNA was used as the input for each reaction. The RNA was first ligated at the 3' end in a 20 µL reaction using T4 RNA Ligase 2 (deleted mutant, Cat# T4RL2T-100, MC Lab, San Francisco, United States) and a pre-adenylated RA3 adapter. For 3' adapter cleanup, one ligation reaction was then subjected to size separation as described in Example 1, using 25% (v/v) ethanol as final binding concentration. For 3' adapter cleanup of the second reaction using blocking oligos, a reverse primer complementary to the RA3 sequence was added to the 3' adaptor ligation. The control blocking method reaction and the column-based removal method reaction of the current invention were then subjected to 5' adapter ligation using T4 RNase Ligase 1 (Cat# T4RL1-100, MC Lab, San Francisco, United States) and RA5 adapter. The final ligated products (RA5-microRNA-RA3) were then subjected to cDNA synthesis using a M-MLV reverse transcriptase (Norgen TruScript Reverse Transcriptase, Cat#54440, Norgen, Thorold, Canada) and reverse primer complementary to the RA3 sequence. This was followed by a limited (15) cycle PCR amplification to enrich the cDNA and also to attach the indexing (barcode) sequences. The indexed libraries were then subjected to clean-up using Norgen's PCR Purification Kit (Cat#14400, Norgen, Thorold, Canada) and resolved on an Agilent High Sensitivity DNA Chip (Cat#5067-4626, Agilent, Santa Clara, United States).

Figure 6:
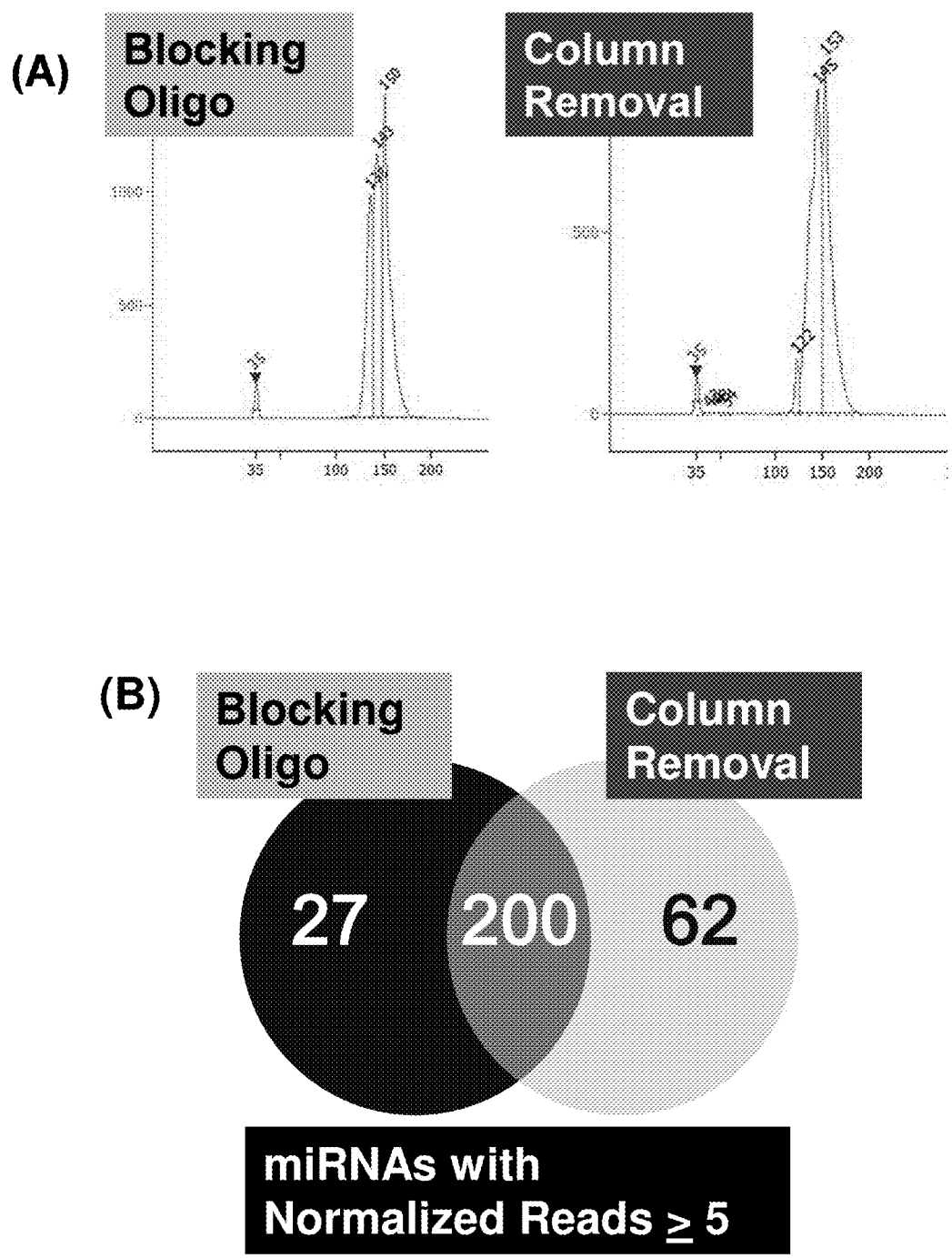
FIG. 6, panel A compares the predominant PCR products obtained for a small RNA library prepared using a blocking oligonucleotide for 3' adapter cleanup (left panel) and a SiC based size exclusion 3' adapter cleanup method as disclosed herein (right panel) prior to PCR amplification.

As shown in FIG. 6, Panel A, both the control/oligo blocking method and the SiC column removal method of the current invention yielded a predominant PCR product of 142-151 bp, typical of the small RNA diversity of plasma RNA. The libraries were sequenced on an Illumina MiSeq sequencer at 50 cycles single read. The resulting reads were mapped to microRNAs using exceRpt small RNA-seq Pipeline (genboree.org/theCommons/projects/exrna-tools-may2014/wiki/Small_RNA-seq_Pipeline).

The Venn diagram (FIG. 6, Panel B) generated using miRNA with reads equal or more than 5 RPM (reads per millions) showed that both methods shared the same diversity of 200 miRNAs. Interestingly, the library generated using the SiC-based column removal method for the 3' adapter cleanup yielded more unique miRNAs (62) than that of the control method based on using blocking oligos (27). This showed that while the SiC-based column removal method does not alter the diversity of miRNA incorporated, it may further enhance the number of different miRNA incorporated into a small RNA sequencing library.

The invention claimed is:

1. A method for isolating nucleic acids having a size above a desired minimum cut-off size from a nucleic acid containing sample, comprising the steps of:
   a) combining the sample with a binding buffer, alcohol and silicon carbide to provide a binding mixture, wherein the nucleic acids having a size above the minimum cut-off size bind to the silicon carbide, and wherein the minimum cut-off size is determined by the alcohol concentration of the binding mixture;
   b) separating the bound nucleic acids from the remaining sample;
   c) optionally, washing the bound nucleic acids; and
   d) eluting the bound nucleic acids from the silicon carbide.

2. The method of claim 1, wherein the alcohol is ethanol, isopropanol or methanol.

3. The method of claim 1, wherein the alcohol is ethanol and wherein the ethanol concentration of the binding buffer and/or the binding mixture is:
   i) at least about 10% (v/v) and the minimum cut-off size is about 43 nucleotides or larger;
   ii) at least about 25% (v/v) and the minimum cut-off size is about 22 nucleotides or larger; or
   ii) at least about 50% (v/v) and the minimum cut-off size is about 10 nucleotides or larger.

4. The method of claim 1, wherein the silicon carbide is provided as a slurry or in a column.

5. The method of claim 1, wherein the nucleic acid is a single stranded RNA, a double stranded RNA, a single stranded DNA, a double stranded DNA or double stranded RNA/DNA hybrid.

6. The method of claim 1, wherein the nucleic acid containing sample comprises:
   i) extracted nucleic acids, which have optionally been subject to mechanical or enzymatic treatment;
   ii) amplification reaction products; and/or
   iii) ligation reaction products.

7. The method of claim 6, where the amplification reaction products are polymerase chain reaction (PCR) products.

8. The method of claim 6, wherein the ligation reaction products are adaptor ligation products, wherein the adaptor ligation products are nucleic acids flanked by 5' and/or 3' adapters; adapter monomers; and/or adapter-adapter ligation products.

9. The method of claim 1, wherein the nucleic acid containing sample was obtained during the preparation of a next generation sequencing library and the nucleic acid containing sample is an adapter ligation sample comprising nucleic acids flanked by 5' and/or 3' adapters; adapter monomers; and/or adapter-adapter ligation products.

10. The method of claim 1, wherein the method is for isolating adapter-ligated RNA molecules from an adapter ligation sample and for removing adapter monomers and adapter-adapter ligation products based on the larger size of the adapter-ligated RNA molecules, and wherein step a) comprises contacting the adapter ligation sample with the binding buffer, alcohol and silicon carbide and binding adapter ligated RNA molecules to the silicon carbide, wherein under the used alcohol concentration, the adapter monomers and adapter-adapter ligation products substantially do not bind to the silicon carbide.

11. The method of claim 10, wherein the minimum cut-off size lies above the size of adapter monomers and above the size of expected adapter-adapter ligation products and wherein the minimum cut-off size is at least 10 nucleotides, at least 15 nucleotides, at least 20 nucleotides, at least 25 nucleotides or at least 30 nucleotides above the size of expected adapter-adapter ligation products.

12. A method for preparing a small RNA library suitable for next generation sequencing, wherein said method comprises
   a) isolating small RNA molecules from a sample;
   b) performing a 3' adapter ligation step to provide a 3' adaptor ligation reaction mixture comprising single stranded small RNA molecules that are flanked 3' by adapters;
   c) isolating single stranded small RNA molecules having a fragment size above a predetermined minimum cut-off size in order to remove 3' adapter monomers and adapter-adapter ligation products, wherein said size selection step comprises:
      i) combining the 3'adaptor ligation reaction mixture with a binding buffer, alcohol and silicon carbide to provide a binding mixture, wherein the single stranded small RNA molecules having a fragment size above the minimum cut-off size bind to the silicon carbide, and wherein the minimum cut-off size is determined by the alcohol concentration of the binding mixture;
      ii) separating the bound single stranded small RNA molecules from the remaining ligation reaction mixture;
      iii) optionally, washing the bound single stranded small RNA molecules; and
      iv) eluting the bound single stranded small RNA molecules from the silicon carbide;
   d) performing a 5' adapter ligation step to provide a 5'adaptor ligation reaction mixture comprising single stranded small RNA molecules that are flanked 3' and 5' by adapters;
   e) optionally, performing a step of isolating single stranded small RNA molecules having a fragment size above a predetermined minimum cut-off size in order to remove 5' adapter monomers and adapter-adapter ligation products, wherein said size selection step comprises:
      i) combining the 5'adaptor ligation reaction mixture with a binding buffer, alcohol and silicon carbide to provide a binding mixture, wherein the single stranded small RNA molecules having a fragment size above the minimum cut-off size bind to the silicon carbide, and wherein the minimum cut-off size is determined by the alcohol concentration of the binding mixture;

ii) separating the bound single stranded small RNA molecules from the remaining ligation reaction mixture;

iii) optionally, washing the bound single stranded small RNA molecules; and iv) eluting the bound single stranded small RNA molecules from the silicon carbide;

f) reverse transcribing single stranded RNA molecules flanked with 5' and 3' adaptors to provide single stranded cDNA molecules; and g) amplifying the single stranded cDNA molecules by limited cycle PCR to incorporate an index sequence.

13. The method of claim 12, wherein the alcohol is ethanol, isopropanol or methanol.

14. The method of claim 12, wherein the alcohol is ethanol and wherein the ethanol concentration of the binding buffer and/or the binding mixture is:

i) at least about 10% (v/v) and the minimum cut-off size is about 43 nucleotides or larger;

ii) at least about 25% (v/v) and the minimum cut-off size is about 22 nucleotides or larger; or iii) at least about 50% (v/v) and the minimum cut-off size is about 10 nucleotides or larger.

15. A method for preparing a small RNA library suitable for next generation sequencing, wherein said method comprises:

a) isolating small RNA molecules from a sample;

b) performing a 5' adapter ligation step to provide a 5' adaptor ligation reaction mixture comprising single stranded small RNA molecules that are flanked 5' by adapters;

c) isolating single stranded small RNA molecules having a fragment size above a predetermined minimum cut-off size in order to remove 5' adapter monomers and adapter-adapter ligation products, wherein said size selection step comprises:

i) combining the 5'adaptor ligation reaction mixture with a binding buffer, alcohol and silicon carbide to provide a binding mixture, wherein the single stranded small RNA molecules having a fragment size above the minimum cut-off size bind to the silicon carbide, and wherein the minimum cut-off size is determined by the alcohol concentration of the binding mixture;

ii) separating the bound single stranded small RNA molecules from the remaining ligation reaction mixture;

iii) optionally, washing the bound single stranded small RNA molecules; and iv) eluting the bound single stranded small RNA molecules from the silicon carbide;

d) performing a 3' adapter ligation step to provide a 3'adaptor ligation reaction mixture comprising single stranded small RNA molecules that are flanked 3' and 5' by adapters;

e) optionally, performing a step of isolating single stranded small RNA molecules having a fragment size above a predetermined minimum cut-off size in order to remove 3' adapter monomers and adapter-adapter ligation products, wherein said size selection step comprises:

i) combining the 3'adaptor ligation reaction mixture with a binding buffer, alcohol and silicon carbide to provide a binding mixture, wherein the single stranded small RNA molecules having a fragment size above the minimum cut-off size bind to the silicon carbide, and wherein the minimum cut-off size is determined by the alcohol concentration of the binding mixture;

ii) separating the bound single stranded small RNA molecules from the remaining ligation reaction mixture;

iii) optionally, washing the bound single stranded small RNA molecules; and iv) eluting the bound single stranded small RNA molecules from the silicon carbide;

f) reverse transcribing single stranded RNA molecules flanked with 5' and 3' adaptors to provide single stranded cDNA molecules; and g) amplifying the single stranded cDNA molecules by limited cycle PCR to incorporate an index sequence.

16. The method of claim 15, wherein the alcohol is ethanol, isopropanol or methanol.

17. The method of claim 16, wherein the alcohol is ethanol and wherein the ethanol concentration of the binding buffer and/or the binding mixture is:

i) at least about 10% (v/v) and the minimum cut-off size is about 43 nucleotides or larger;

ii) at least about 25% (v/v) and the minimum cut-off size is about 22 nucleotides or larger; or iii) at least about 50% (v/v) and the minimum cut-off size is about 10 nucleotides or larger.

18. A kit for the selective binding of nucleic acids having a size above a desired minimum cut-off size, comprising:

a) a binding buffer to be combined with ethanol to provide an ethanol concentration of about 1 to about 50% (v/v);

b) a wash solution;

c) an elution solution;

d) silicon carbide; and e) instructions for adjusting the ethanol concentration to selectively bind nucleic acids having a size above the desired minimum cut-off size;

wherein the minimum cut-off size is at least about 10 nucleotides.

19. The kit according to claim 18, wherein the silicon carbide is provided as a slurry or in a column.

20. The kit according to claim 18, wherein i) the ethanol concentration is at least about 10% (v/v) and the minimum cut-off size is about 43 nucleotides or larger;

ii) the ethanol concentration is at least about 25% (v/v) and the minimum cut-off size is about 22 nucleotides or larger; or iii) the ethanol concentration is about 50% (v/v) and the minimum cut-off size is about 10 nucleotides or larger.

* * * * *

SEQUENCE LISTING

```
<160> NUMBER OF SEQ ID NOS: 5

<210> SEQ ID NO 1
<211> LENGTH: 22
<212> TYPE: RNA
<213> ORGANISM: Artificial Sequence
<220> FEATURE:
<223> OTHER INFORMATION: cel-miR-39

<400> SEQUENCE: 1 ucaccggguguaaaucagcu ug                                             22

<210> SEQ ID NO 2
<211> LENGTH: 21
<212> TYPE: DNA
<213> ORGANISM: Artificial Sequence
<220> FEATURE:
<223> OTHER INFORMATION: 3' Adapter sequence RA3

<400> SEQUENCE: 2
tggaattctc gggtgccaag g                                             21

<210> SEQ ID NO 3
<211> LENGTH: 43
<212> TYPE: DNA
<213> ORGANISM: Artificial Sequence
<220> FEATURE:
<223> OTHER INFORMATION: cel-miR-39-RA3

<400> SEQUENCE: 3 ucaccggguguaaaucagcu ugtggaattc tcgggtgcca agg                      43

<210> SEQ ID NO 4
<211> LENGTH: 26
<212> TYPE: RNA
<213> ORGANISM: Artificial Sequence
<220> FEATURE:
<223> OTHER INFORMATION: 5' Adapter sequence RA5

<400> SEQUENCE: 4
guucagaguu cuacaguccg acgauc                                        26

<210> SEQ ID NO 5
<211> LENGTH: 69
<212> TYPE: DNA
<213> ORGANISM: Artificial Sequence
<220> FEATURE:
<223> OTHER INFORMATION: RA5-cel-miR-39-RA3
```

```
<400> SEQUENCE: 5
guucagaguu cuacaguccg acgaucucac cggguguaaa ucagcuugtg gaattctcgg    60
gtgccaagg                                                           69
```